(12) United States Patent
Kobsiriphat et al.

(10) Patent No.: US 8,623,197 B1
(45) Date of Patent: Jan. 7, 2014

(54) TESTING WORKPIECE OVERCOAT

(75) Inventors: Worawarit Kobsiriphat, Klong Luang (TH); Laddawan Supadee, Paktor (TH); Krisda Siangchaew, Muang (TH)

(73) Assignee: Western Digital (Fremont), LLC, Fremont, CA (US)

( * ) Notice: Subject to any disclaimer, the term of this patent is extended or adjusted under 35 U.S.C. 154(b) by 146 days.

(21) Appl. No.: 12/973,032

(22) Filed: Dec. 20, 2010

(51) Int. Cl.
*C23F 13/04* (2006.01)

(52) U.S. Cl.
USPC ....... 205/777.5; 204/404; 205/777; 324/71.2; 324/693; 324/700; 73/83

(58) Field of Classification Search
USPC ................ 204/404; 205/775.5–777; 73/86; 324/71.2, 693, 700
See application file for complete search history.

(56) References Cited

U.S. PATENT DOCUMENTS

| | | | | |
|---|---|---|---|---|
| 3,813,240 A | * | 5/1974 | Abe | 420/42 |
| 4,806,849 A | | 2/1989 | Kihira et al. | |
| 4,839,593 A | * | 6/1989 | Spies | 324/240 |
| 5,370,776 A | * | 12/1994 | Chen | 205/776.5 |
| 5,660,695 A | | 8/1997 | Mahvan et al. | |
| 5,864,452 A | * | 1/1999 | Hirano et al. | 360/122 |
| 6,313,647 B1 | | 11/2001 | Feng et al. | |
| 6,369,589 B1 | * | 4/2002 | Gao et al. | 324/693 |
| 6,512,382 B1 | | 1/2003 | Hsiao et al. | |
| 2005/0036242 A1 | * | 2/2005 | Sato | 360/319 |
| 2008/0179198 A1 | * | 7/2008 | Burgess et al. | 205/775.5 |
| 2009/0238952 A1 | | 9/2009 | Kubo et al. | |

OTHER PUBLICATIONS

Shitanda, I., Okumura, A., Itagaki, M., Watanabe, K., Asano, Y., Screen-printed Atmospheric Corrosion Monitoring Sensor based on Electrochemical Impedance Spectroscopy, 2009, Sensors and Actuators B, 139, 292-297.*

* cited by examiner

*Primary Examiner* — Bach Dinh

(57) ABSTRACT

A method and apparatus for testing workpiece overcoats is described.

19 Claims, 6 Drawing Sheets

TESTING WORKPIECE OVERCOAT

TECHNICAL FIELD

Embodiments described herein relate to the field of workpiece processing, and, in particular, to testing a workpiece overcoat.

BACKGROUND

Surface materials of workpieces may be adversely affected by corrosive environments in various different industries. In the petroleum industry, corrosion of metallic surfaces by petroleum materials occurs at different stages of production and distribution. To reduce this corrosion, inhibitors have been utilized as a corrosion control method. There are various inhibitors which work in different ways, as well as various screening procedures used for the selection of inhibitors. Some inhibitors work by neutralizing active ions, others by reducing ion mobility and others by changing the ion transport numbers. In all cases the electrical conductivity of the corrosive fluid is altered, and various electrical parameters contributing to the overall corrosion mechanism will be affected. Accordingly, by using the corrosive fluid as an electrolyte in which two electrodes are immersed, and by measuring electrical characteristics of the electrolytic circuit, an indication of the level of corrosion which continues to occur may be derived. U.S. Pat. No. 5,370,776 describes a technique that utilizes the "break point frequency" (frequency at 45° phase angle) in order to determine the effectiveness of a corrosion inhibitor in preventing corrosion of metallic surfaces using electrochemical impedance spectroscopy (EIS).

In the magnetic recording industry, one corrosion auditing technique uses a scanning electronic microscope (SEM) to visually evaluate overcoat materials. Such a visual technique is time consuming and can sometimes yield false positives.

Another corrosion evaluation technique, used in the magnetic recording industry, is described in U.S. Pat. No. 6,512,382. Magnetic heads coated with diamond-like carbon films are tested by exposing the heads to a salt environment similar to that found in a production process. By comparing the sensor resistance values measured immediately following salt application and after exposure under different conditions (varying temperature, humidity and time), the susceptibility of the magnetic head to corrosion is determined.

Yet another solution, though not specifically for magnetic heads, is described in U.S. Pat. No. 4,806,849. The degradation level of a sample is determined by first dividing the sample into several zones using a grid. Impedance spectra are obtained from each area, and the degree of degradation is ranked based on the statistical distribution of the measured impedance values.

BRIEF DESCRIPTION OF THE DRAWINGS

The present invention is illustrated by way of example, and not limitation, in the figures of the accompanying drawings in which.

DETAILED DESCRIPTION

Embodiments of a method are described herein with reference to figures. However, particular embodiments may be practiced without one or more of these specific details, or in combination with other known methods, materials, and apparatuses. In the following description, numerous specific details are set forth, such as specific materials, dimensions and processes parameters etc. to provide a thorough understanding. In other instances, well-known manufacturing processes and equipment have not been described in particular detail to avoid unnecessarily obscuring the claimed subject matter. Reference throughout this specification to "an embodiment" means that a particular feature, structure, material, or characteristic described in connection with the embodiment is included in at least one embodiment of the invention. Thus, the appearances of the phrase "in an embodiment" in various places throughout this specification are not necessarily referring to the same embodiment. Furthermore, the particular features, structures, materials, or characteristics may be combined in any suitable manner in one or more embodiments.

Embodiments of a method are described for determining the relative abilities of an overcoat (e.g., carbon) to protect a workpiece (e.g., AlTiC substrate) from exposure to a corrosive environment (e.g., an acid or salt solution) that may cause damage to the workpiece. A method of evaluating the workpiece overcoat includes the use of electrochemical impedance spectroscopy to measure the electrochemical properties of the overcoated workpiece. Information extracted from the impedance data is used to determine the level of protection that is provided by the overcoat.

In one embodiment, the evaluation method includes submerging the workpiece having an overcoat in an electrochemical cell comprising a corrosive fluid. A circuit path is established in the electrochemical cell using the workpiece as a working electrode and a reference electrode disposed in the corrosive fluid. An excitation signal is applied at one or more frequencies to the circuit path and then a normalized modulus of impedance value is determined at one or more time points.

For ease of understanding the context of the present invention, embodiments are described in which the workpiece is a wafer composed of a ceramic aluminum titanium carbide (AlTiC) substrate with a carbon overcoat, out of which head sliders are formed for use in a magnetic recording disk Although embodiments of the present invention are described in the context of magnetic recording head wafers, it should be appreciated that embodiments of the present invention may also be used with optical disks, semiconductor wafers, photomasks, glass substrates, flat panel display surfaces, liquid crystal display surfaces or other types of workpieces.

Figure 1A:
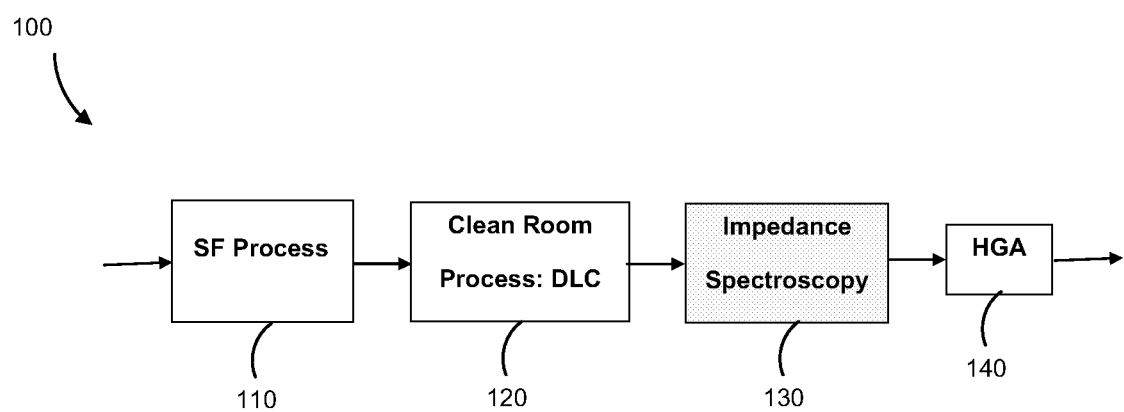
FIG. 1A illustrates a process flow of performing impedance spectroscopy measurements in-line with a workpiece manufacturing process, according to one embodiment of the present invention.
Figure 2:
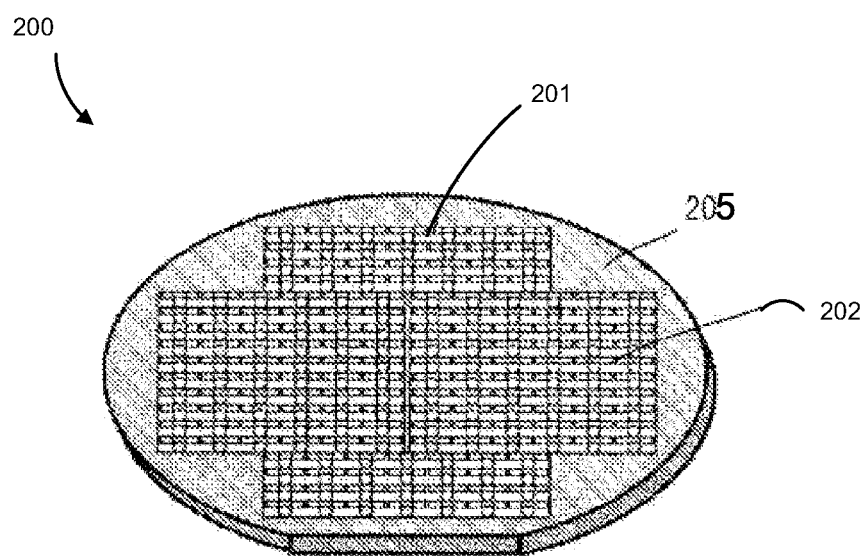
FIG. 2 illustrates one embodiment of a workpiece and corresponding overcoat.

FIG. 1A illustrates part of a head manufacturing process 100, according to one embodiment of the present invention. In current disk drive systems that employ flying heads, a read/write head is used to read and write data on a magnetic recording disk or medium. The read/write head element is typically a part of or affixed to a larger body that flies over the disk and is typically referred to as a "slider." Accordingly, the head may also be referred to as a head slider. The head sliders are fabricated as device arrays in wafer form, process 110, using techniques that are well known in the art; according a detailed description is not provided herein. In one embodiment, the wafer substrate 220 may be composed of AlTiC on which the head sliders will be formed as illustrated in FIG. 2. As can be seen in FIG. 2, multiple head sliders (e.g., 201 and 202) are formed on the AlTiC substrate 200 having an overcoat 205 disposed thereon.

Referring again to FIG. 1A, the outer surface of the head slider wafers are coated with an overcoat material or protective film, operation 120. In one embodiment, the overcoat is composed of diamond like carbon (DLC). Alternatively, the overcoat may be composed of other materials, for examples, alumina ($Al_2O_3$), Silicon (Si), etc.

Figure 1B:
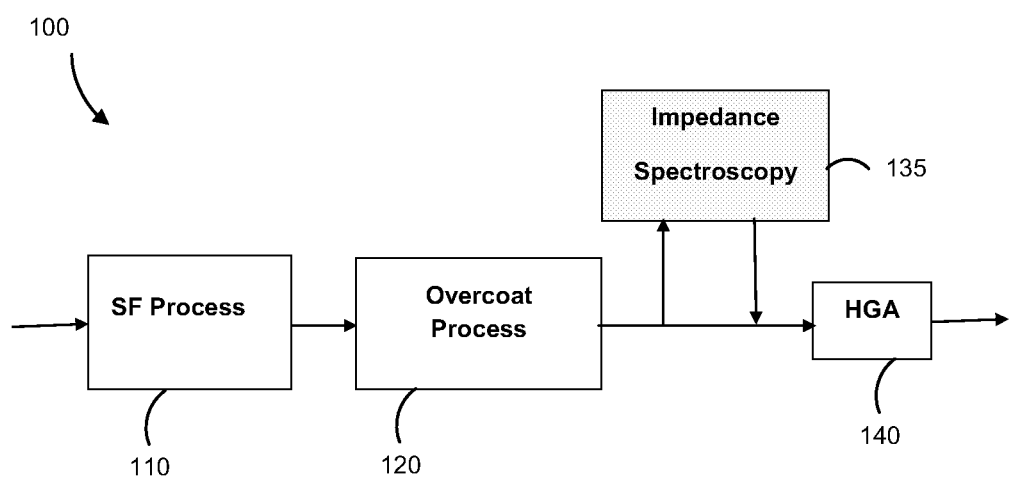
FIG. 1B illustrates a process flow of performing impedance spectroscopy measurements off-line with a workpiece manufacturing process, according to an alternative embodiment of the present invention.

After a wafer has been coated, the overcoat of the wafer may be tested for corrosion susceptibility using electrochemical impedance spectroscopy, operation 130, as described in more detail below. After testing, the wafer is sent to head gimbal assembly (HGA), operation 140, in which the wafer is cut up to manufacture the individual head slider assemblies. In the embodiment illustrated in FIG. 1A, all wafers may be evaluated in-line before being sent to HGA. Alternatively, a sample of wafers may be selected for impedance spectroscopy testing off-line, operation 135, as illustrated in FIG. 1B.

Figure 3:
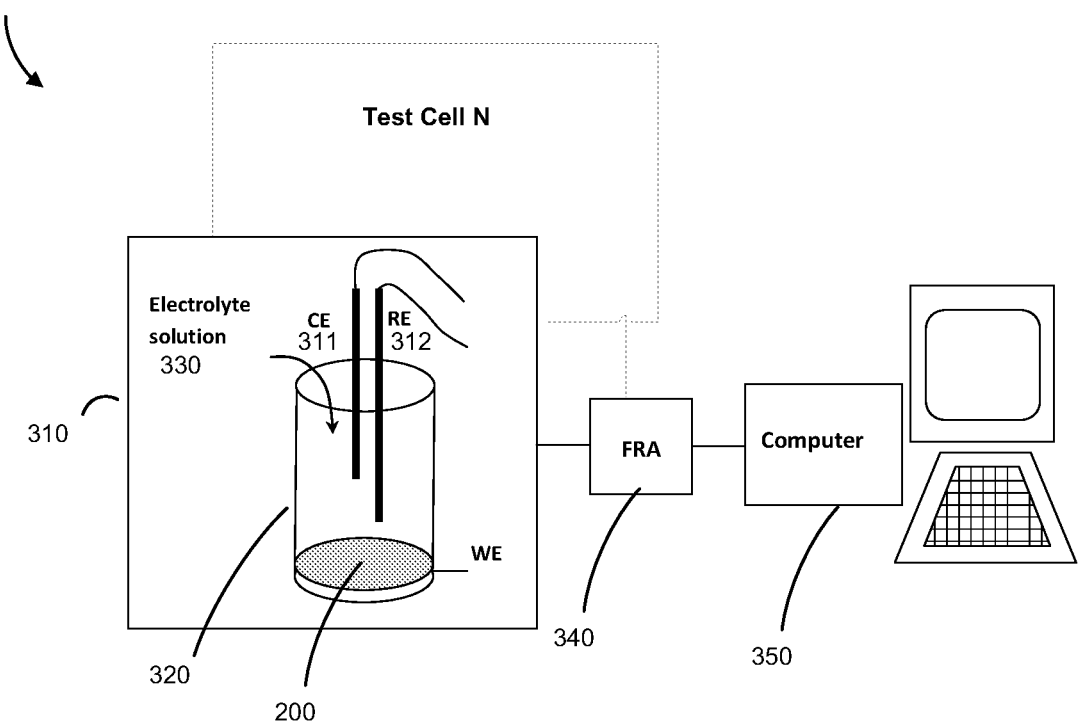
FIG. 3 illustrates one embodiment of an impedance spectroscopy measurement system.
Figure 4:
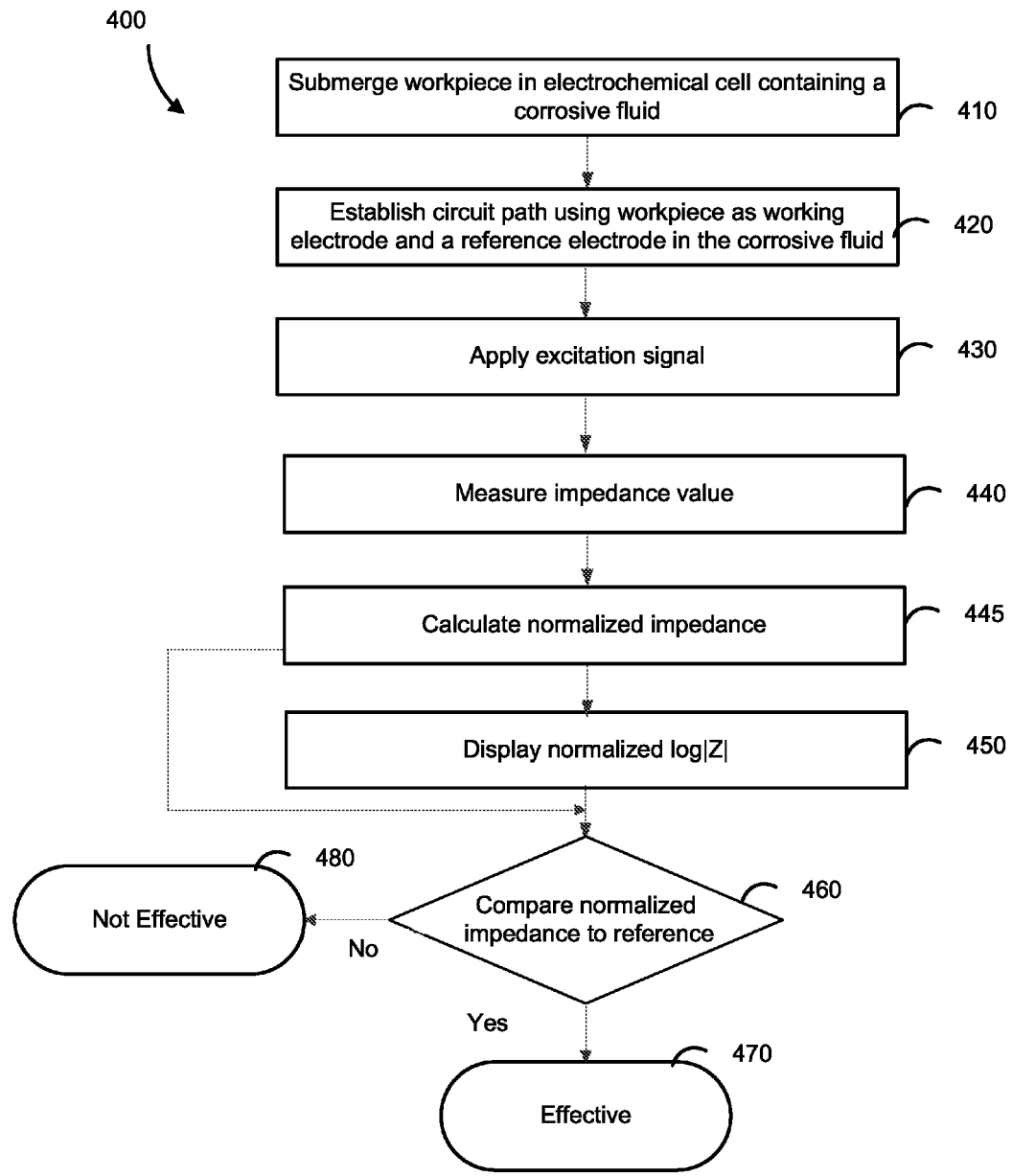
FIG. 4 illustrates one embodiment of a method evaluating a workpiece overcoat.

FIG. 3 illustrates one embodiment of an impedance spectroscopy measurement system and FIG. 4 illustrates one embodiment of a method evaluating a workpiece overcoat. Reference is made to both FIGS. 3 and 4 in discussion of the operation of the system and testing methodology. In one embodiment, impedance spectroscopy measurement system 300 includes a test cell 310, a high frequency impedance analyzer 340, and a computer 350. It should be noted that although only a single test cell is discussed, multiple (e.g., N number of test cells) may be connected to FRA 340. A workpiece 200 is submerged in electrochemical test cell 310 containing an aqueous electrolyte solution of corrosive fluid 330 in container 320, block 410 of FIG. 4. In one embodiment, the electrolyte solution 330 electrolyte solution is an 0.5 M $H_2SO_4$ solution. Alternatively, other corrosive solutions may be used. The submerged workpiece 200 operates as a working electrode (WE). A reference electrode (RE) lead 311 and a counter electrode (CE) lead 312 are submerged into the solution 330 in order to establish a circuit path in the electrochemical cell 310, block 420 of FIG. 4. Once the setup is in place, an excitation signal at one or more frequencies is applied through the circuit path with FRA 340, block 430 of FIG. 4. In one embodiment, an open circuit potential may be obtained after allowing the workpiece to equilibrate in the electrolyte solution for a time period (e.g., 60 seconds). The excitation signal may have an amplitude of 5 millivolts (mV) and a frequency in a range of 1 Hertz (Hz) to 10 Hz. IT should be noted that the test parameters provide herein are only examples and, in alternative embodiments, other test parameters may be used.

In block 440 of FIG. 4, a modulus of impedance value is measured using FRA 340 and computer 350 at one or more time points (e.g., 60 points distributed logarithmically over a period of 100 seconds). In one embodiment, the measurements may be performed at standard ambient temperature and pressure. Impedance measurement software running on computer 350 may be used to display the measured impedance data, for example, in the form of a Bode plot. The Bode plot, which can be used for data comparison, plots the modulus of impedance (log|Z|) in $\Omega cm^2$ as a function of log (frequency) in Hz as illustrated in FIG. 5.

Figure 5:
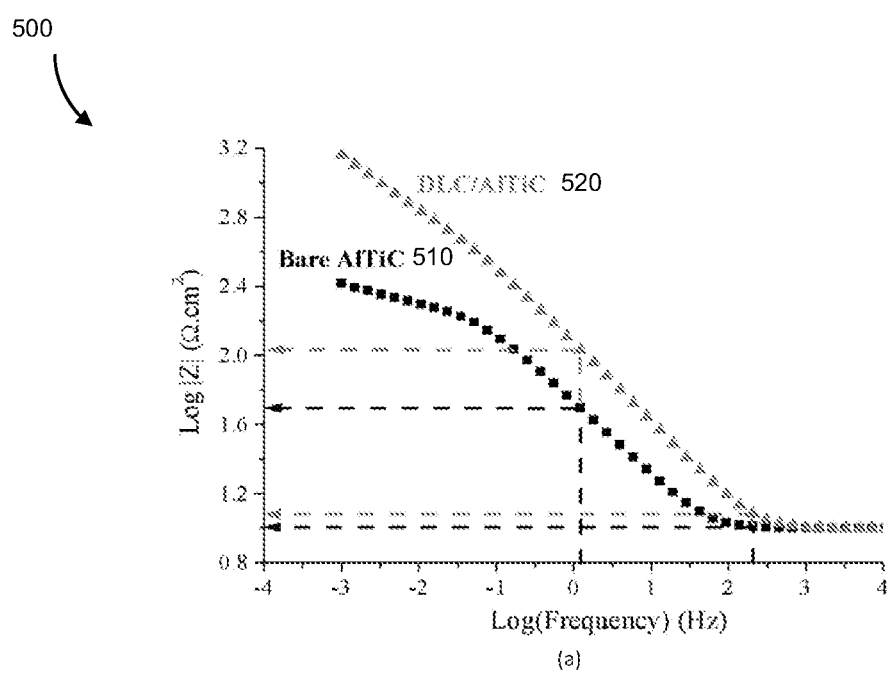
FIG. 5 is a Bode plot illustrating a comparison of impedance spectra obtained from a bare AlTiC wafer and an AlTiC wafer coated with DLC, according to one embodiment of the present invention.

The Bode plot 500 of FIG. 5 illustrates a comparison of impedance spectra obtained from a bare AlTiC wafer (square data points 510) and an AlTiC wafer coated with DLC (triangular data points 520). The impedance modules vs. log (frequency) plot shows that a DLC coated AlTiC wafer has higher impedance moduli at frequencies equal to $10^{0.085}$ and $10^{2.313}$ Hz.

Referring again to FIG. 4, for each spectrum, the modulus of impedance, |Z| may be normalized in one embodiment, block 445, by setting log(|Z|) at frequency=$10^4$ Hz to unity, i.e., divide all log(|Z|) values by the value of log(|Z|) (frequency=$10^4$ Hz). This step sets the ohmic resistance, which originates from the electrolyte, to approximately the same value in all tested workpieces. This will enable direct comparison of the measured impedance values. The following value from the plots after normalization are recorded and may be displayed to the user in operation 450: log(|Z|) at frequency=$10^0$ Hz. This frequency may be used in one embodiment because the ohmic effects (flat portion at high frequency in log(|Z|) vs. frequency plots) do not extend to this frequency in any of the workpiece samples plotted in FIG. 5. The ohmic portion of the plot is attributable to the electrolyte, not the workpiece itself. The frequency chosen is not at too low a value, thus the time required to make the measurement is sufficiently short. In alternative embodiments, the normalized impedance values are not displayed to the user. For example, software on computer 350 may automatically determine and identify an acceptable workpiece based on predetermined comparison metrics as discussed in further detail below.

The overcoat on a workpiece that has a high value of log(|Z|) at $10^0$ Hz is considered to provide better protection than that of the other workpiece. For example, in one embodiment, a standard or reference normalized modulus of impedance value may be established through empirical data and used as a metric by which workpieces are compared against to determine if they are considered satisfactory. For example, the data plotted in FIG. 5 may indicated that log|Z|=1.8 ohm $cm^2$ may be used as a standard, or reference, value in one embodiment. Of course, this value is only an example and would be based on workpiece parameters, experimental conditions, observations, etc.

In one embodiment, to determine whether the overcoat is effective in preventing the workpiece from exposure to the electrolyte, the log|$Z_{work\ piece}$| (at $10^0$ Hz) value is compared to the average log|$Z_{substrate}$| (at $10^0$ Hz) of a reference workpiece that is the same as the tested workpiece but without the overcoat and tested in the same electrolyte solution, block 460. This log|$Z_{substrate}$| value is obtained from separate (e.g., prior) measurements and is to be used as a reference value. If log|$Z_{work\ piece}$| of the tested workpiece is greater than the log|$Z_{substrate}$| of the reference workpiece, then the overcoat is determined to be effective in protecting the substrate of the tested workpiece, block 470. If log|$Z_{work\ piece}$| of the tested workpiece is less than the log|$Z_{substrate}$| of the reference workpiece, then the overcoat is determined to be ineffective in protecting the substrate, block 480. The larger the difference between the log|Z| of the test workpiece and the reference value, the more effective the overcoat as a barrier.

The advantages of embodiments of the present invention over conventional solutions for corrosion auditing may include: 1) smaller measurement time and 2) lower cost. In one embodiment, the test cell 310 may be designed such that the corrosive solution and electrodes remain in place and only the workpiece 200 need to be changed, further reducing the sample preparation/mounting time.

It should be noted that embodiments of the present invention are not limited to characterization of carbon coatings on AlTiC substrates. Embodiments of the present invention may also be used to characterize other types of workpieces having other types of overcoats. Examples of other types of overcoats and substrates include, but are not limited to, diamond-like carbon (DLC) film on Mg alloys, DLC on stainless steel (e.g., for biomedical applications), $Al_2O_3$ on aluminum alloys, chromium-, titanium-, aluminum- and zirconium nitride on stainless steel. The frequency value used to compare the sample quality should be adjusted accordingly, based on experimental observations. The frequency chosen should be away from any ohmic effects from the electrolyte, typically observed at high frequency. In an embodiment, the frequency chosen frequency is not too low as to significantly prolong the measurement time.

Moreover, the measurement of impedance characteristics of a workpiece are not limited to just evaluating the ability of an overcoat (e.g., carbon) to protect a workpiece from exposure to a corrosive environment. In addition to effectiveness in evaluating corrosion susceptibility, the impedance characteristics of a workpiece, such as $\log(|Z|)$ at $10^0$ Hz, can be related to other properties. For example, $\log(|Z|)$ at $10^0$ Hz may be correlated (at least qualitatively) to properties such as refractive index (n,k), Raman peak intensity and wear resistance of a workpiece.

In the foregoing specification, the present invention has been described with reference to specific exemplary embodiments thereof. It will, however, be evident that various modifications and changes may be made thereto without departing from the broader scope of the embodiments of the invention as set for in the appended claims. For example, although steps of embodiments of inventive methods may have been described in a specific order, one of skill in the art will understand that some of the steps described may occur simultaneously, in overlapping time frames, and/or in a different order from that described and claimed herein and fall within embodiments of the present invention. The specification and drawings are, accordingly, to be regarded in an illustrative rather than a restrictive sense.

What is claimed is:

1. A method of evaluating an overcoat on a workpiece, the workpiece having the overcoat prior to the method of evaluating the overcoat being performed, the method of evaluating the overcoat comprising:
   submerging the workpiece having the overcoat in an electrochemical cell comprising a corrosive fluid;
   establishing a circuit path in the electrochemical cell using the workpiece as a working electrode and a reference electrode disposed in the corrosive fluid;
   applying an excitation signal at one or more frequencies to the circuit path;
   measuring a modulus of impedance value for one or more frequencies within a range of 1 Hz to 10 Hz at one or more time points; and
   dividing the measured modulus of impedance value by a high frequency modulus of impedance value measured at a frequency above 10 Hz to generate a normalized modulus of impedance value.

2. The method of claim 1, further comprising displaying the normalized modulus of impedance value.

3. The method of claim 2, wherein the normalized modulus of impedance value is measured using a frequency response analyzer coupled to the electrochemical cell and displayed on a display of a computer operative coupled to the frequency response analyzer.

4. The method of claim 1, wherein the normalized modulus of impedance value ($\log|Z|$) is at a fixed frequency of 1 Hertz.

5. The method of claim 1, wherein the high frequency modulus of impedance value is measured at a frequency of $10^4$ Hz.

6. The method of claim 1, further comprising:
   setting a reference value; and
   determining if the normalized modulus of impedance ($\log|Z|$) value is above the reference value.

7. The method of claim 6, wherein the reference value is an average $\log|Z|$ of a reference workpiece, without the overcoat, when submerged in the corrosive fluid and evaluated using the excitation signal.

8. The method of claim 1, further comprising determining an effectiveness of the overcoat to prevent corrosion of the workpiece based on the normalized modulus of impedance value.

9. The method of claim 1, wherein the overcoat comprises carbon.

10. The method of claim 9, wherein the workpiece is a magnetic recording head wafer that comprises an aluminum titanium carbide (AlTiC) substrate.

11. The method of claim 9, wherein the overcoat has a thickness in a range of 10 Angstroms to 30 Angstroms.

12. The method of claim 1, wherein the corrosive fluid is an electrolyte solution.

13. The method of claim 1, wherein the corrosive fluid is a solution that includes $H_2SO_4$.

14. The method of claim 1, wherein the circuit path has an open circuit potential after allowing the workpiece to equilibrate in the corrosive fluid for a time period.

15. The method of claim 14, wherein the excitation signal has an amplitude of 5 mV and the normalized modulus of impedance value is measured at ambient temperature and pressure.

16. An electrochemical impedance spectroscopy measurement system, comprising:
   an electrochemical cell containing a corrosive fluid and a submerged workpiece having an overcoat;
   a circuit path in the electrochemical cell that includes the workpiece as a working electrode and a reference electrode disposed in the corrosive fluid;
   a frequency response analyzer that applies an excitation signal at one or more frequencies to the circuit path;
   the frequency response analyzer being electrically coupled to the circuit path and measuring a modulus of impedance value for one or more frequencies within a range of 1 Hz to 10 Hz at one or more time points; and
   a computer that is coupled to the frequency response analyzer and configured to normalize the measured modulus of impedance value by dividing the measured modulus of impedance value by a high frequency modulus of impedance value measured at a frequency above 10 Hz.

17. The electromechanical impedance spectroscopy measurement system of claim 16, further comprising a display of the normalized modulus of impedance value.

18. The electromechanical impedance spectroscopy measurement system of claim 16, wherein the high frequency modulus of impedance value is measured at a frequency of $10^4$ Hz.

19. The electromechanical impedance spectroscopy measurement system of claim 16, wherein the overcoat is a carbon overcoat.

* * * * *